United States Patent
Mikami et al.

(10) Patent No.: US 12,133,027 B2
(45) Date of Patent: Oct. 29, 2024

(54) MEDICAL CONTROL DEVICE AND MEDICAL OBSERVATION CONTROLLING PROJECTED ILLUMINATION

(71) Applicant: Sony Olympus Medical Solutions Inc., Tokyo (JP)

(72) Inventors: Takamasa Mikami, Tokyo (JP); Tatsuya Deguchi, Tokyo (JP)

(73) Assignee: Sony Olympus Medical Solutions Inc., Tokyo (JP)

( * ) Notice: Subject to any disclaimer, the term of this patent is extended or adjusted under 35 U.S.C. 154(b) by 330 days.

(21) Appl. No.: 17/437,843

(22) PCT Filed: Jan. 10, 2020

(86) PCT No.: PCT/JP2020/000748
§ 371 (c)(1),
(2) Date: Sep. 10, 2021

(87) PCT Pub. No.: WO2020/188969
PCT Pub. Date: Sep. 24, 2020

(65) Prior Publication Data
US 2022/0151460 A1    May 19, 2022

(30) Foreign Application Priority Data

Mar. 19, 2019   (JP) ................. 2019-051417

(51) Int. Cl.
*A61B 1/00* (2006.01)
*A61B 1/045* (2006.01)
(Continued)

(52) U.S. Cl.
CPC ......... *H04N 7/183* (2013.01); *A61B 1/00006* (2013.01); *A61B 1/000095* (2022.02);
(Continued)

(58) Field of Classification Search
CPC ....... A61B 1/06; A61B 1/0638; A61B 1/0661; A61B 1/0655; A61B 1/00009;
(Continued)

(56) References Cited

U.S. PATENT DOCUMENTS

2009/0149713 A1   6/2009  Niida
2010/0134608 A1*  6/2010  Shibasaki ............. H04N 23/71
                                              348/E7.085
(Continued)

FOREIGN PATENT DOCUMENTS

JP   2001-235686 A   8/2001
JP   2002-159445 A   6/2002
(Continued)

OTHER PUBLICATIONS

International Search Report and Written Opinion mailed on Mar. 31, 2020, received for PCT Application PCT/JP2020/000748, Filed on Jan. 10, 2020, 9 pages including English Translation.

*Primary Examiner* — John W Miller
*Assistant Examiner* — Humam M Satti
(74) *Attorney, Agent, or Firm* — XSENSUS LLP

(57) ABSTRACT

A medical control device according to the present disclosure includes an image processing section adapted to generate a captured image on the basis of an electric signal generated by an imaging device that captures an image of a subject, and a light source control information generation section adapted to generate control information for controlling a light quantity distribution of illumination light, according to a brightness distribution of the captured image.

5 Claims, 12 Drawing Sheets

(51) Int. Cl.
*A61B 1/06* (2006.01)
*G02B 23/26* (2006.01)
*H04N 7/18* (2006.01)
*H04N 23/50* (2023.01)

(52) U.S. Cl.
CPC ............ *A61B 1/045* (2013.01); *A61B 1/0605* (2022.02); *A61B 1/0655* (2022.02); *G02B 23/26* (2013.01); *H04N 7/18* (2013.01); *H04N 23/555* (2023.01)

(58) Field of Classification Search
CPC . A61B 1/000095; A61B 1/0005; A61B 1/043; A61B 1/00006; A61B 1/045; A61B 1/0605; H04N 7/183; H04N 7/18; H04N 23/555; G02B 23/26; G02B 21/0012; G02B 21/361; G02B 21/367; G02B 23/2415; G02B 23/2469; G02B 2207/113
See application file for complete search history.

(56) References Cited

U.S. PATENT DOCUMENTS

| | | | |
|---|---|---|---|
| 2011/0071352 A1* | 3/2011 | Ozawa | A61B 1/0669 |
| | | | 600/109 |
| 2014/0152790 A1* | 6/2014 | Saito | A61B 5/1459 |
| | | | 348/68 |
| 2016/0374545 A1 | 12/2016 | Obara | |
| 2016/0381273 A1* | 12/2016 | Honda | H04N 23/76 |
| | | | 348/69 |

FOREIGN PATENT DOCUMENTS

| | | |
|---|---|---|
| JP | 2017-119146 A | 7/2017 |
| JP | 2018-500995 A | 1/2018 |
| WO | WO-2018235166 A1 | 12/2018 |

\* cited by examiner

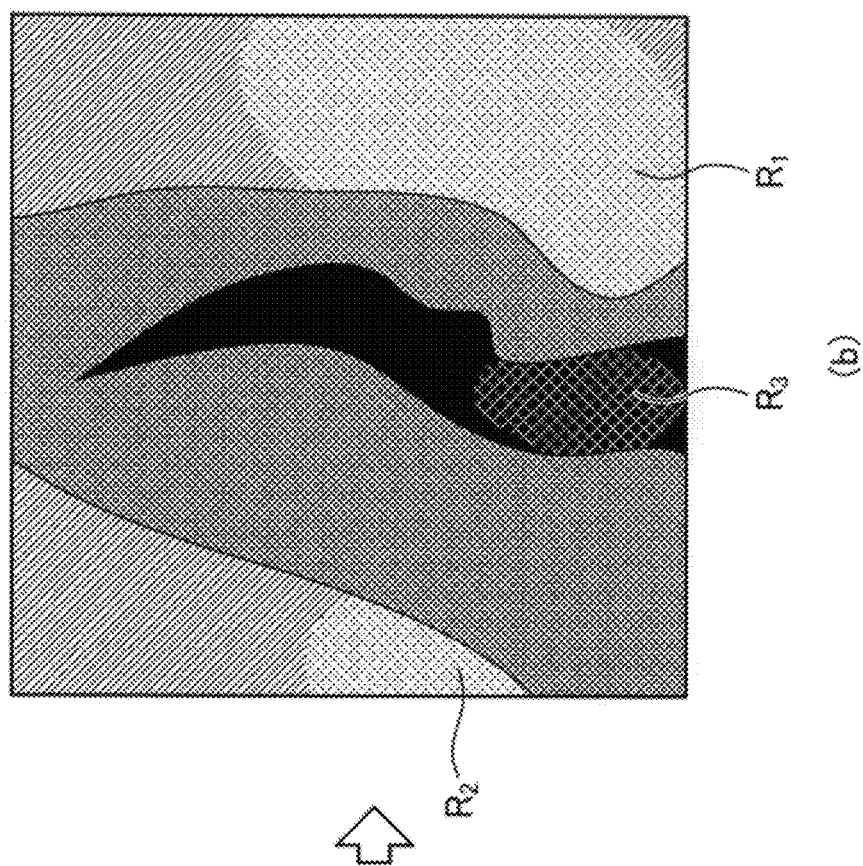
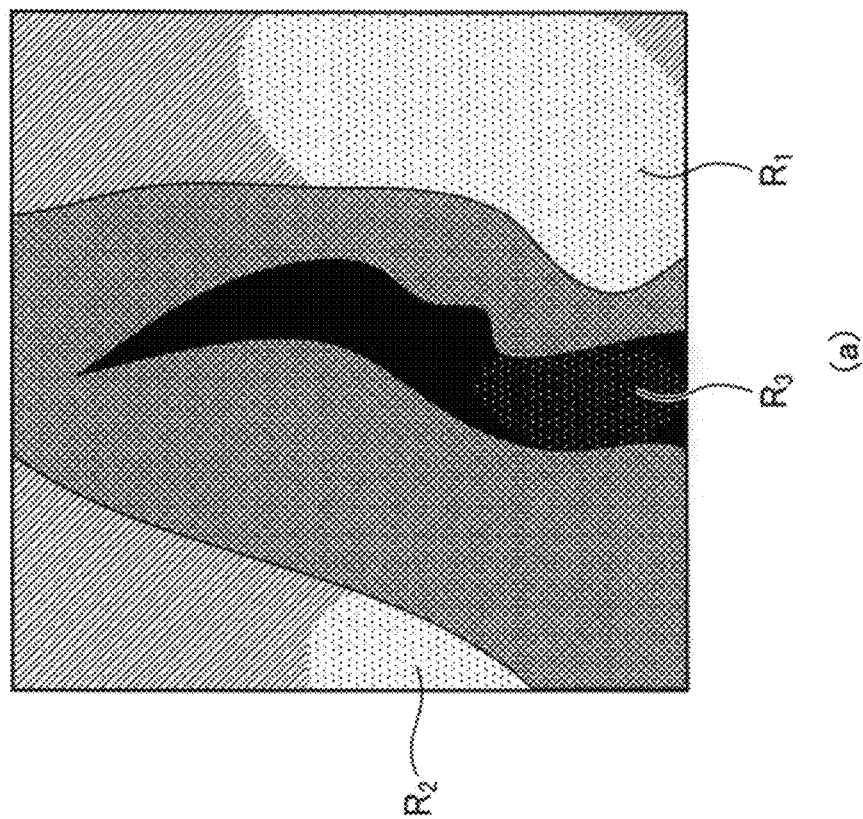
FIG. 5

FIG.9
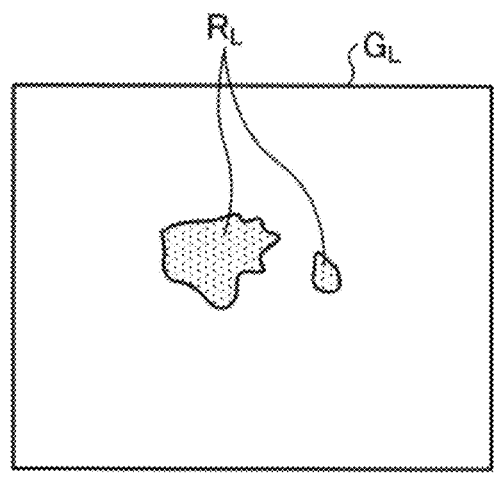
(a)
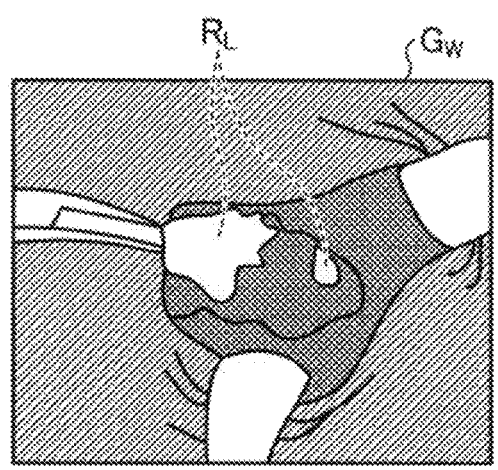
(b)
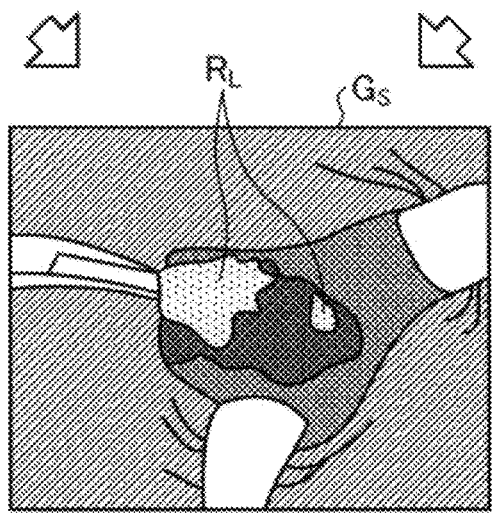
(c)

MEDICAL CONTROL DEVICE AND MEDICAL OBSERVATION CONTROLLING PROJECTED ILLUMINATION

CROSS-REFERENCE TO RELATED APPLICATIONS

The present application is based on PCT filing PCT/JP2020/000748, filed Jan. 10, 2020, which claims priority to JP 2019-051417, filed Mar. 19, 2019, the entire contents of each are incorporated herein by reference.

TECHNICAL FIELD

The present disclosure relates to a medical control device and a medical observation apparatus.

BACKGROUND ART

In medical and industrial fields, an endoscope apparatus that captures an image of a subject by using imaging elements, a medical microscope apparatus, and other medical apparatuses are known (refer, for example, to PTL 1). Of these, the endoscope apparatus includes, for example, an endoscope, an imaging device, a display device, a control device, and a light source device. In the endoscope apparatus, illumination light is supplied from the light source device via a light guide that is connected to the endoscope, and the subject image is captured by being irradiated with the illumination light.

When a stereoscopic structure is observed using the endoscope, it may be impossible to strike a balance in brightness between a near point and a far point due to surface irregularities of the structure, resulting in partial overbrightness or darkness. The light source device disclosed in PTL 1 has a plurality of LED light sources and changes a light quantity distribution of light emitted from the light source device by controlling the light quantity emitted from each of the light sources. It is possible to adjust a difference in partial brightness between the near point and the far point by controlling the light quantity distribution.

CITATION LIST

Patent Literature

[PTL 1]
Japanese Patent Laid-Open No. 2002-159445

SUMMARY

Technical Problem

However, the light quantity distribution that can be controlled by a single LED light source is limited, and a technique has been demanded to allow more elaborate adjustment of the light quantity distribution so as to clarify an image of a complex stereoscopic structure.

The present disclosure has been devised in light of the foregoing problem, and it is an object of the present disclosure to provide a medical control device and a medical observation apparatus that allow elaborate control over the light quantity distribution of illumination light irradiated on the subject.

Solution to Problem

In order to solve the above problem and achieve the object, a medical control device according to the present disclosure includes an image processing section adapted to generate a captured image on the basis of an electric signal generated by an imaging device that captures an image of a subject, and a light source control information generation section adapted to generate control information for controlling a light quantity distribution of illumination light, according to a brightness distribution of the captured image.

Also, in the medical control device according to the present disclosure, in the above disclosure, the light source control information generation section converts the captured image generated by the image processing section to generate irradiation distribution information indicating the light quantity distribution of the illumination light according to the brightness distribution of the captured image.

Also, in the medical control device according to the present disclosure, in the above disclosure, the light source control information generation section converts the captured image into a luminance image having a luminance value assigned to each pixel and generates, as the irradiation distribution information, an irradiation image in which a projection luminance of a region in which the luminance value is larger than a first threshold is decreased to below a reference luminance set in advance and a projection luminance of a region in which the luminance value is smaller than a second threshold is increased to above the reference luminance.

Also, in the medical control device according to the present disclosure, in the above disclosure, the light source control information generation section converts a special light image captured with special light into a luminance image having a luminance value assigned to each pixel and generates an irradiation image as the irradiation distribution information by inverting the luminance image such that, in the irradiation image a region in which a luminance value after the inversion is larger than a third threshold is set as a white light projection region, and the image processing section generates a merged image obtained by merging the special light image and a white light image captured with white light whose light quantity distribution is commensurate with the irradiation image.

Also, a medical observation apparatus according to the present disclosure includes an imaging section adapted to generate an electric signal by capturing an image of a subject, an image processing section adapted to generate a captured image on the basis of the electric signal generated by the imaging section, a light source control information generation section adapted to generate control information for controlling a light quantity distribution of illumination light, according to a brightness distribution of the captured image, a light source section having a light source that emits light and a projection element that externally projects the light emitted by the light source according to the control information, and a light source control section adapted to control emission of illumination light by the light source section on the basis of the control information.

Also, the medical observation apparatus according to the present disclosure includes, in the above disclosure, a first light source section having a first light source that emits white light and a projection element that externally projects the light emitted by the first light source according to the control information, and a second light source section having a second light source that emits special light. The light source control information generation section generates the control information for setting a projection region of the white light on the basis of a special light image captured by the imaging section with the special light.

Also, the medical observation apparatus according to the present disclosure includes, in the above disclosure, a base light source section adapted to emit white light.

Advantageous Effect of Invention

The present disclosure provides an advantageous effect of elaborately controlling a light quantity distribution of illumination light irradiated on a subject.

BRIEF DESCRIPTION OF DRAWINGS

FIG. 5 is a diagram schematically illustrating examples of images before and after illumination light emission control.

FIG. 9 is a diagram schematically illustrating examples of images resulting from illumination light emission control.

DESCRIPTION OF EMBODIMENTS

A description will be given below of modes for carrying out the present disclosure (hereinafter referred to as "embodiments"). In the embodiments, a description will be given of a medical endoscope apparatus that captures an image inside a test subject such as a patient, as an example of a system including a medical observation apparatus according to the present disclosure. Also, this disclosure is not limited by these embodiments. Further, in the description of drawings, the same portions will be denoted by the same reference signs for description.

Embodiment 1

Figure 1:
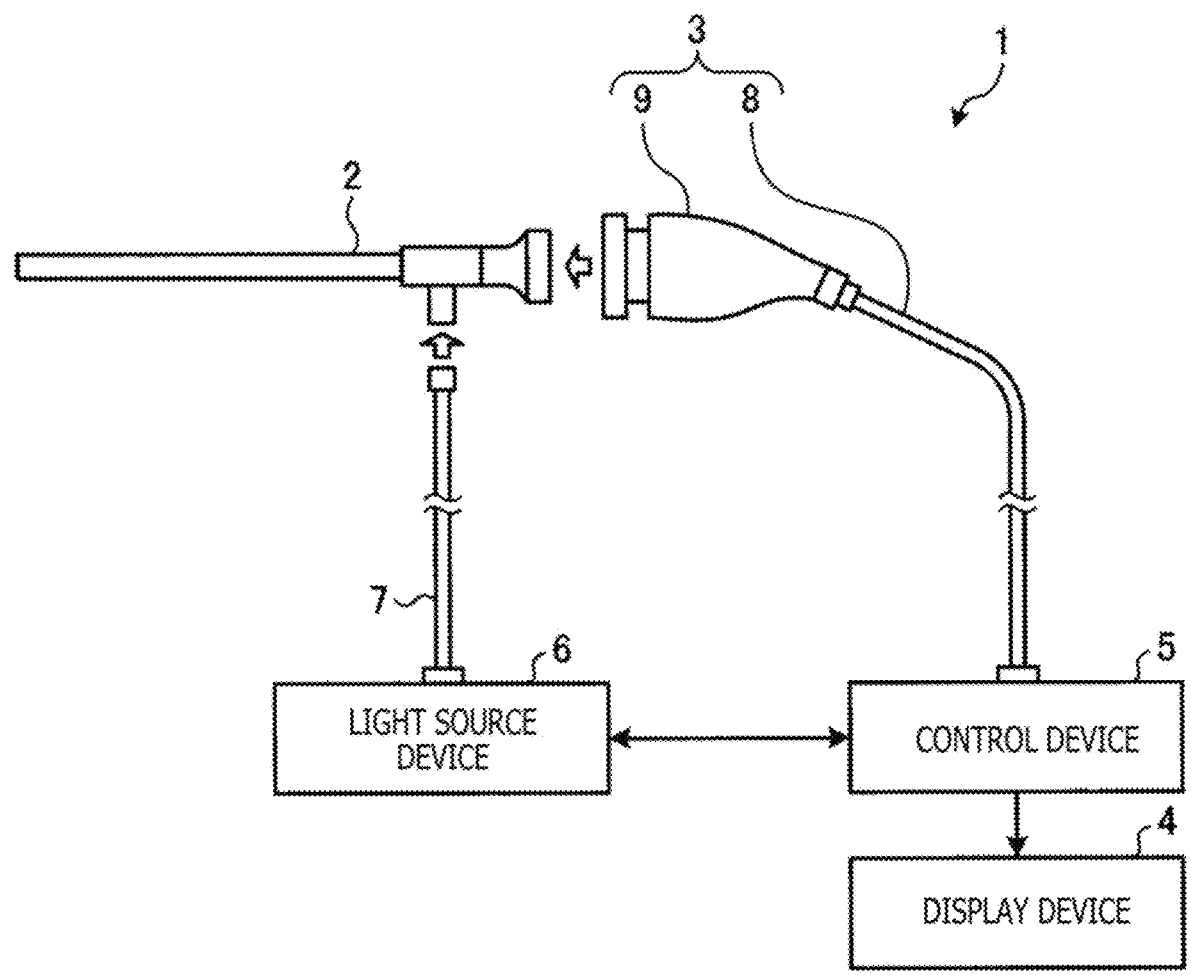
FIG. 1 is a diagram illustrating a schematic configuration of an endoscope apparatus according to embodiment 1.

FIG. 1 is a diagram illustrating a schematic configuration of an endoscope apparatus 1 according to embodiment 1. The endoscope apparatus 1 is used in a medical field to observe a subject inside a target to be observed such as a human (inside a living body). The endoscope apparatus 1 includes an endoscope 2, an imaging device 3, a display device 4, a control device 5, and a light source device 6 as illustrated in FIG. 1, and the imaging device 3 and the control device 5 configure a medical observation system. It should be noted that the endoscope 2 and the imaging device 3 configure an image acquisition device that uses, for example, an endoscope such as a rigid scope.

One end of a light guide 7 is connected to the light source device 6, and the light source device 6 supplies, for example, white light for illuminating the inside of the living body to the one end of the light guide 7. It should be noted that the light source device 6 and the control device 5 may be separate from each other as illustrated in FIG. 1 and communicate with each other or may be integral with each other.

The light guide 7 has its one end detachably connected to the light source device 6 and its other end detachably connected to the endoscope 2. Then, the light guide 7 transmits light supplied from the light source device 6 from its one end to its other end, thus supplying the light to the endoscope 2.

The imaging device 3 captures a subject image from the endoscope 2 and outputs a result of this imaging. The imaging device 3 includes a transmission cable 8, which is a signal transmission section, and a camera head 9. In the present embodiment 1, the transmission cable 8 and the camera head 9 configure a medical imaging device. The imaging device 3 corresponds to an imaging section.

The endoscope 2 is rigid, long and narrow in shape, and inserted into the living body. An observation optical system that includes one or a plurality of lenses and collects light to form a subject image is provided inside the endoscope 2. The endoscope 2 emits light supplied via the light guide 7 from its tip to irradiate the inside of the living body with the light. Then, the light irradiated inside the living body (subject image) is collected by the observation optical system (lens unit 91) inside the endoscope 2.

The camera head 9 is detachably connected to a base end of the endoscope 2. Then, the camera head 9 captures the subject image formed by collecting light with the endoscope 2 and outputs an imaging signal resulting from this imaging, under control of the control device 5. It should be noted that the detailed configuration of the camera head 9 will be described later. The endoscope 2 and the camera head 9 may be detachable from each other as illustrated in FIG. 1 or may be integral with each other.

The transmission cable 8 has its one end detachably connected to the control device 5 via a connector and its other end detachably connected to the camera head 9 via a connector. Specifically, the transmission cable 8 is a cable that has a plurality of electric wires (not illustrated) arranged inside an outer cover which is an outermost layer. The plurality of electric wires is used to transmit the imaging signal output from the camera head 9 to the control device 5 and transmit a control signal, a synchronizing signal, a clock, and power output from the control device 5 to the camera head 9.

The display device 4 displays an image generated by the control device 5, under control of the control device 5. Although the display device 4 having a display section of 55 inches or more is preferred to make it easier for one to feel a sense of immersion during observation, the display device 4 is not limited thereto.

The control device 5 processes the imaging signal input from the camera head 9 via the transmission cable 8, outputs an image signal to the display device 4, and comprehensively controls operation of the camera head 9 and the display device 4. It should be noted that the detailed configuration of the control device 5 will be described later.

Figure 2:
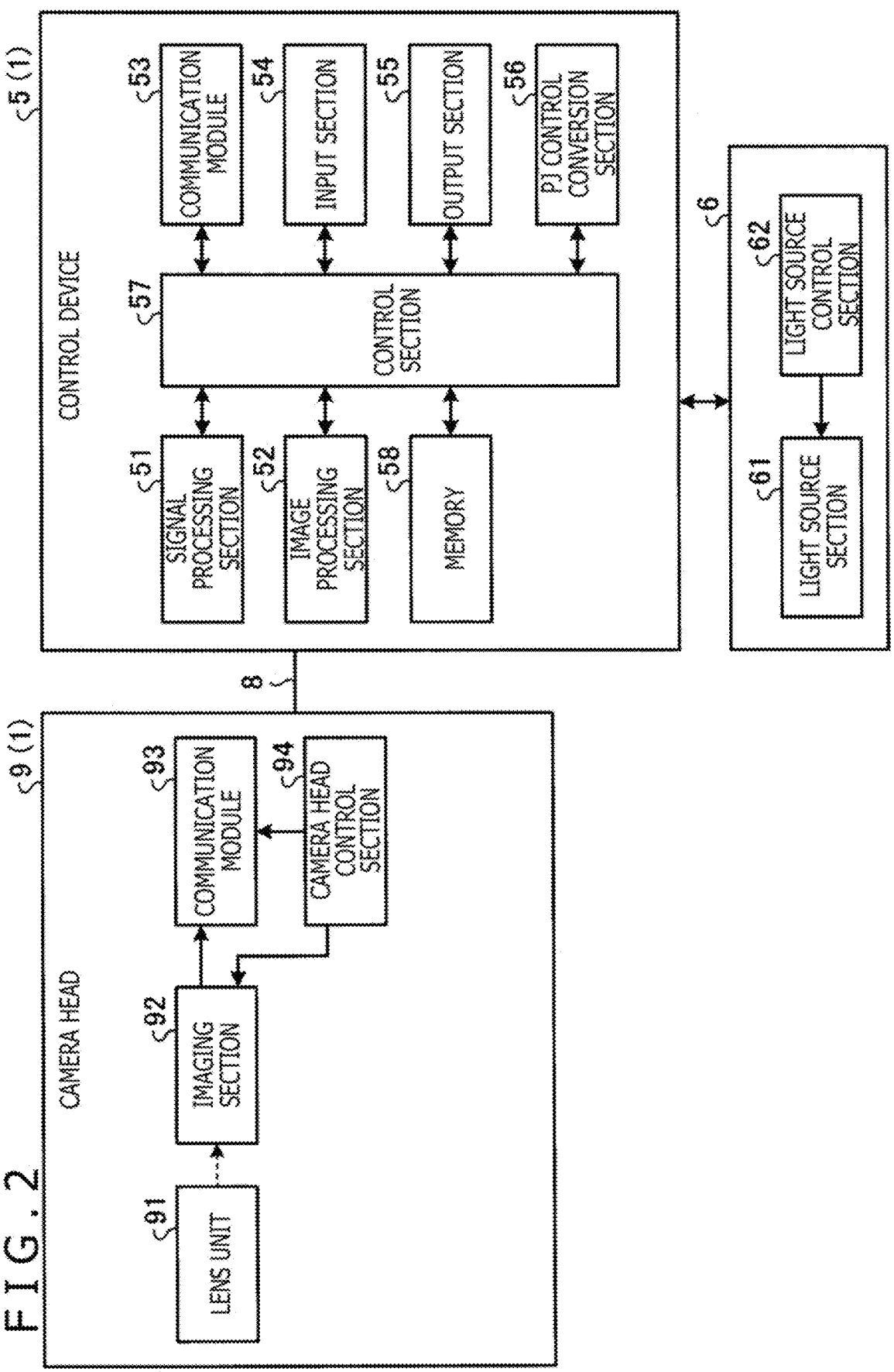
FIG. 2 is a block diagram illustrating configurations of a camera head, a control device, and a light source device illustrated in FIG. 1.

A description will be given next of configurations of the imaging device 3, the control device 5, and the light source device 6. FIG. 2 is a block diagram illustrating the configurations of the camera head 9, the control device 5, and the light source device 6. It should be noted that the connector that allows the camera head 9 and the transmission cable 8 to be attached to and detached from each other is not illustrated in FIG. 2.

A description will be given below of the configurations of the control device 5 and the camera head 9 in this order. It should be noted that essential parts of the present disclosure will be mainly described below as the configuration of the control device 5. The control device 5 includes a signal processing section 51, an image processing section 52, a communication module 53, an input section 54, an output section 55, a projector control conversion section (PJ control conversion section) 56, a control section 57, and a memory 58 as illustrated in FIG. 2. It should be noted that a power supply section (not illustrated) or the like may be provided in the control device 5. The power supply section generates a source voltage for driving the control device 5 and the camera head 9 and supplies the source voltage to different sections of the control device 5 and to the camera head 9 via the transmission cable 8. It should be noted that the control device that controls the light source device 6 includes the image processing section 52 and the PJ control conversion section 56.

The signal processing section 51 outputs an imaging signal (pulse signal) to the image processing section 52. The imaging signal has been digitized as a result of signal processing such as noise removal and, as necessary, A/D conversion performed on an imaging signal output from the camera head 9.

Also, the signal processing section 51 generates a synchronizing signal and a clock for the imaging device 3 and the control device 5. The synchronizing signal (e.g., a synchronizing signal that indicates an imaging timing for the camera head 9) and the clock (e.g., a serial communication clock) are sent to the imaging device 3 through a line which is not illustrated, and the imaging device 3 is driven on the basis of the synchronizing signal and the clock.

The image processing section 52 generates a display image signal to be displayed by the display device 4 on the basis of the imaging signal input from the signal processing section 51. The image processing section 52 generates the display image signal including a subject image by performing given signal processing on the imaging signal. Here, the image processing section 52 performs known image processing such as various kinds of image processing such as detection processing, interpolation processing, color correction processing, color enhancement processing, and contour enhancement processing. The image processing section 52 outputs the generated image signal to the display device 4 and the PJ control conversion section 56.

The communication module 53 outputs signals from the control device 5, including a control signal sent from the control section 57 which will be described later, to the imaging device 3. Also, the communication module 53 outputs signals from the imaging device 3 to different sections of the control device 5. That is, the communication module 53 is a relay device that collectively outputs signals from different sections of the control device 5 to be output to the imaging device 3, for example, by parallel-to-serial conversion or other means and divides signals input from the imaging device 3, for example, by serial-to-parallel conversion or other means to output the divided signals to different sections of the control device 5.

The input section 54 is realized by using user interfaces such as a keyboard, a mouse, and to ouch panel and accepts inputs of various kinds of information.

The output section 55 is realized by using a speaker, a printer, a display, and the like and outputs various kinds of information. The output section 55 outputs an alarm sound and alarm light and displays an image under control of the control section 57.

Figure 3:
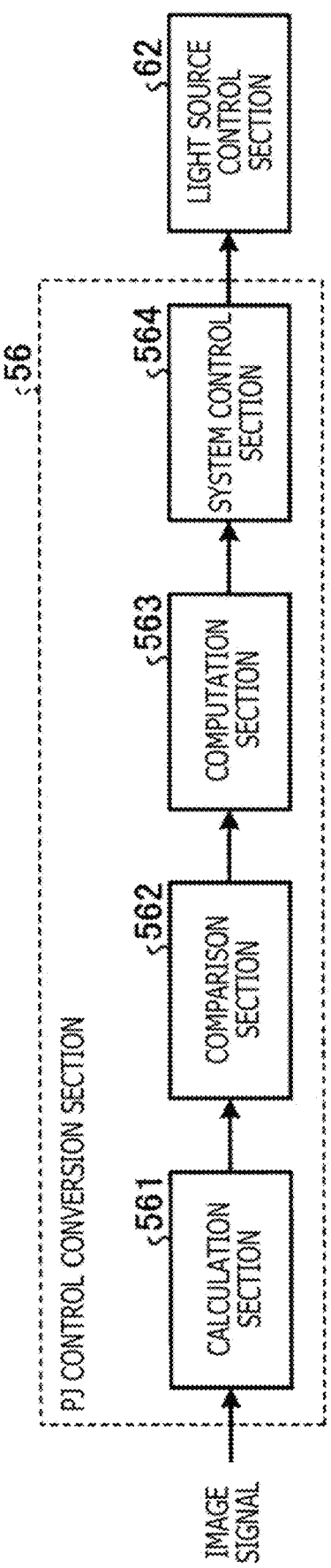
FIG. 3 is a diagram illustrating a configuration of a PJ control conversion section of the control device illustrated in FIG. 2.

The PJ control conversion section 56 generates a control signal for controlling the light source device 6 by converting an image signal generated by the image processing section 52. FIG. 3 is a diagram illustrating a configuration of the PJ control conversion section of the control device illustrated in FIG. 2. The PJ control conversion section 56 includes a calculation section 561, a comparison section 562, a computation section 563, and a system control section 564. The PJ control conversion section 56 corresponds to a light source control information generation section.

The calculation section 561 calculates a luminance value at each pixel position by converting the image signal. The calculation section 561 generates a luminance image having a luminance value assigned to each pixel position on the basis of the calculated luminance value.

The comparison section 562 generates a differential image by comparing the luminance image and a reference image set in advance. The reference image is an image having a target luminance value (reference luminance value) corresponding to a light quantity suitable for irradiation assigned to each pixel position. The differential image is an image having a differential value in luminance value between the luminance image and the reference image assigned to each pixel position.

The computation section 563 generates an irradiation image corresponding to a distribution of illumination light emitted by the light source device 6, on the basis of the differential image. The computation section 563 extracts, with respect to the luminance values of the differential image, pixels having a differential value above an upper limit target value and pixels having a differential value below a lower limit target value. Here, the upper limit target value is a value related to a differential value set in advance and corresponds to a first threshold set on the basis of a differential value by which the light quantity of illumination light is to be decreased. Also, the lower limit target value is a value related to a differential value set in advance and corresponds to a second threshold set on the basis of a differential value by which the light quantity of the illumination light is to be increased.

The computation section 563 subtracts, among the extracted pixels, the differential value from the target luminance value of the reference image for the pixels that exceed the upper limit target value. In contrast, the computation section 563 adds, among the extracted pixels, the differential value to the target luminance value of the reference image for the pixels that fall below the lower limit target value.

As described above, the computation section 563 generates the irradiation image by performing subtraction from the target luminance value for the pixel positions where the luminance values of the acquired image signal are high and by performing addition to the target luminance value for the pixel positions where the luminance values are low. The irradiation image corresponds to irradiation distribution information indicating the light quantity distribution of the illumination light of the light source device 6.

The system control section 564 controls the light source device 6 by outputting the irradiation image generated by the computation section 563 to a light source control section 62.

The control section 57 controls driving of respective sections including the control device 5 and the camera head 9 and controls input and output of information to and from the respective sections. The control section 57 generates a control signal by referencing communication information data (e.g., communication format information) recorded in the memory 58 and sends the generated control signal to the imaging device 3 via the communication module 53. Also, the control section 57 outputs the control signal to the camera head 9 via the transmission cable 8.

The memory 58 is realized by using a semiconductor memory such as a flash memory or a DRAM (Dynamic Random Access Memory) and has communication information data (e.g., communication format information) recorded therein. It should be noted that the memory 58 may have various programs and the like to be executed by the control section 57 recorded therein.

It should be noted that the signal processing section 51 may have an AF processing section and an AF computation section. The AF processing section outputs, on the basis of imaging signals of input frames, a given AF evaluation value for each frame. The AF computation section performs such AF computation processing as to select a frame, a focusing lens position, or the like most suited as a focusing position, from the AF evaluation values of the frames output from the AF processing section.

The signal processing section 51, the image processing section 52, the communication module 53, the PJ control conversion section 56, and the control section 57 described above are realized by using a general-purpose processor such as a CPU (Central Processing Unit) having an internal memory (not illustrated) in which programs are recorded or a dedicated processor such as various arithmetic circuits for performing specific functions such as an ASIC (Application Specific Integrated Circuit). Also, these sections may include an FPGA (Field Programmable Gate Array: not illustrated) which is a type of programmable integrated circuit. It should be noted that, in the case where the FPGA is used, a memory may be provided to store configuration data such that the FPGA, a programmable integrated circuit, is configured with the configuration data read from the memory.

One end of the light guide 7 is connected to the light source device 6, and the light source device 6 includes a light source section 61 and the light source control section 62. The light source section 61 supplies, for example, white light for illuminating the inside of the living body to the one end of the light guide 7. The light source control section 62 controls emission of illumination light by the light source section 61. It should be noted that the light source device 6 and the control device 5 may be separate from each other as illustrated in FIG. 1 and communicate with each other or may be integral with each other.

The light source section 61 includes a projector light source. The projector light source includes a light source, a projection element, and an optical system. The light source emits white light. The projection element is a digital mirror device (DMD), a liquid crystal panel, or the like. The optical system emits projected light externally. The light source section 61 allows adjustment of a projected image of the projection element under control of the light source control section 62. An adjustment capability of the projection element is determined by the number of pixels each of which includes a set of subpixels that respectively pass red (R), green (G), and blue (B) light, for example, in the case of a liquid crystal panel.

The light source control section 62 causes the light source to emit white light and controls a light projection (emission) pattern of the projection element to match the irradiation image acquired from the system control section 564 on the basis of an instruction from the system control section 564. This provides a brightness (light quantity) distribution of the illumination light emitted from the light source device 6 that is commensurate with the irradiation image.

A description will be given next mainly of essential parts of the present disclosure as the configuration of the camera head 9. The camera head 9 includes the lens unit 91, an imaging section 92, a communication module 93, and a camera head control section 94 as illustrated in FIG. 2.

The lens unit 91 includes one or a plurality of lenses and forms a subject image that has passed through the lens unit 91 on an imaging plane of an imaging element included in the imaging section 92. The one or plurality of lenses is configured in such a manner as to be able to move along an optical axis. Then, the lens unit 91 has an optical zoom mechanism (not illustrated) that changes an angle of view by moving the one or plurality of lenses and a focus mechanism that changes a focus position. It should be noted that the lens unit 91 forms, together with the optical system provided in the endoscope 2, an observation optical system that guides observation light entering the endoscope 2 into the imaging section 92.

The imaging section 92 captures an image of the subject under control of the camera head control section 94. The imaging section 92 includes an imaging element that receives the subject image formed by the lens unit 91 and converts the image into an electric signal. The imaging element includes a CCD (Charge Coupled Device) image sensor or a CMOS (Complementary Metal Oxide Semiconductor) image sensor. In a case where the imaging element is a CCD, a signal processing section (not illustrated) that performs signal processing (e.g., A/D conversion) on an electric signal (analog signal) from the imaging element and outputs an imaging signal is, for example, mounted on a sensor chip or the like. In a case where the imaging element is a CMOS, a signal processing section (not illustrated) that performs signal processing (e.g., A/D conversion) on an electric signal (analog signal) obtained by conversion from light into the electric signal and outputs an imaging signal is, for example, included in the imaging element. The imaging section 92 outputs the generated electric signal to the communication module 93.

The number of pixels of the image sensor of the imaging section 92 is preferably the same as the number of pixels of the projection element of the light source section 61.

The communication module 93 outputs signals sent from the control device 5 to different sections of the camera head 9 such as the camera head control section 94. Also, the communication module 93 converts information regarding a current state of the camera head 9 and the like into a signal format according to a predetermined transmission scheme and outputs signals obtained by this conversion to the control device 5 via the transmission cable 8. That is, the communication module 93 is a relay device that divides signals input from the control device 5 or the transmission cable 8, for example, by serial-to-parallel conversion or other means to output the divided signals to the different sections of the camera head 9 and collectively outputs signals from different sections of the camera head 9 to be output to the control device 5 or the transmission cable 8, for example, by parallel-to-serial conversion or other means.

The camera head control section 94 controls operation of the camera head 9 as a whole according to a drive signal input via the transmission cable 8 or an instruction signal or the like output from a manipulation section such as a switch provided on an external surface of the camera head 9 as a result of a user manipulation made to the manipulation section. Also, the camera head control section 94 outputs information regarding the current state of the camera head 9 to the control device 5 via the transmission cable 8.

It should be noted that the communication module 93 and the camera head control section 94 described above are realized by using a general-purpose processor such as a CPU having an internal memory (not illustrated) in which programs are recorded or a dedicated processor such as various arithmetic circuits for performing specific functions such as an ASIC. Also, these sections may include an FPGA which is a type of programmable integrated circuit. It should be noted that, in the case where the FPGA is used, a memory may be provided to store configuration data such that the FPGA which is a programmable integrated circuit is configured with the configuration data read from the memory.

Also, a signal processing section may be configured in the camera head 9 or the transmission cable 8 to perform signal processing on an imaging signal generated by the communication module 93 or the imaging section 92. Further, an imaging clock for driving the imaging section 92 and a control clock for the camera head control section 94 may be generated on the basis of a reference clock generated by an oscillator (not illustrated) which is provided inside the camera head 9 and output to the imaging section 92 and the camera head control section 94, respectively. Alternatively, timing signals for various kinds of processing of the imaging section 92 and the camera head control section 94 may be generated on the basis of a synchronizing signal input from the control device 5 via the transmission cable 8 and output to the imaging section 92 and the camera head control section 94, respectively. Also, the camera head control section 94 may be provided in the transmission cable 8 or the control device 5 rather than in the camera head 9.

In the endoscope apparatus 1 described above, an image based on an electric signal captured by the imaging section 92 is displayed on the display device 4, and an image signal displayed on the display device 4 is input to the PJ control conversion section 56, thus allowing feedback control to be performed on the light source device 6.

Figure 4:
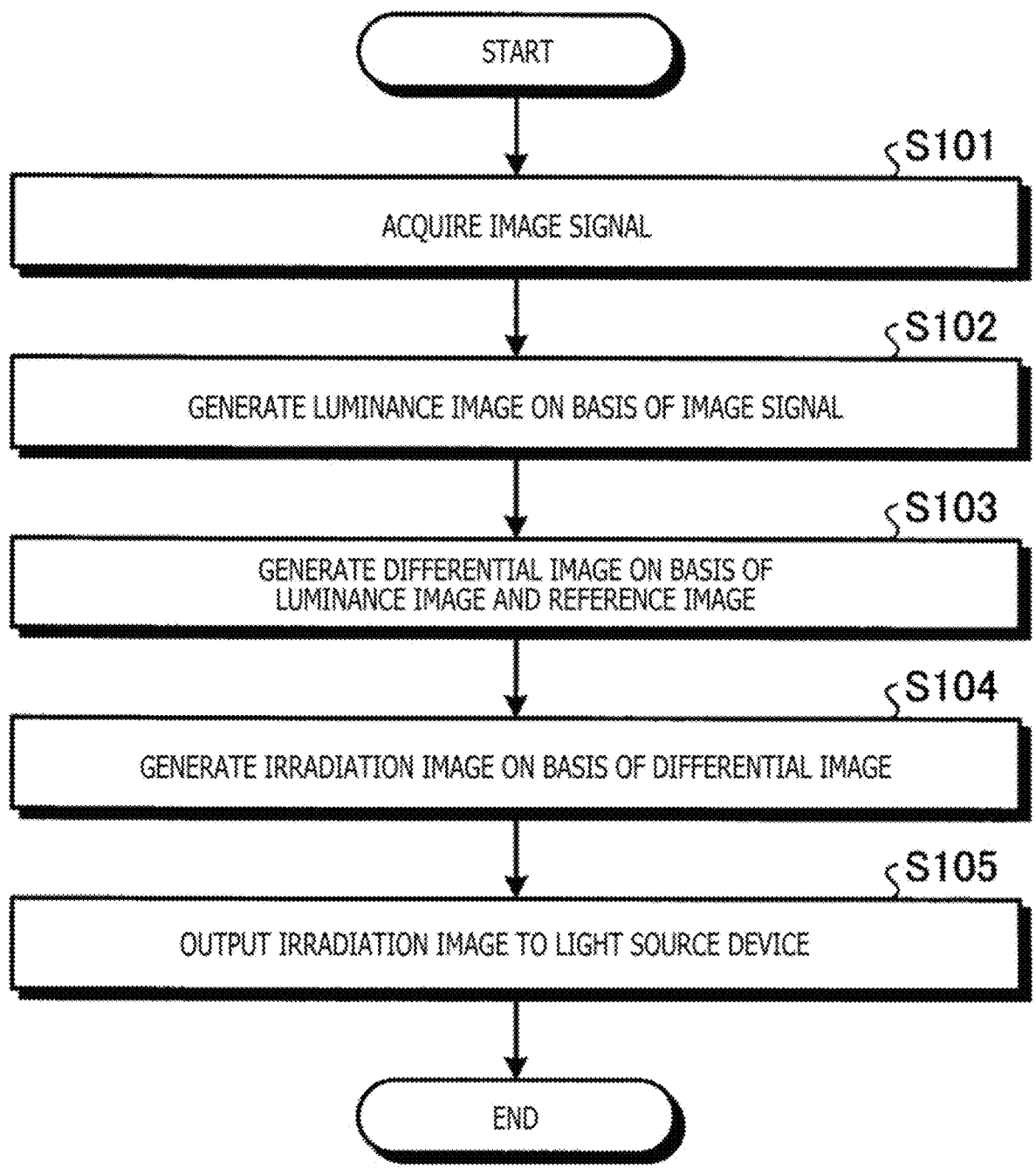
FIG. 4 is flowchart outlining processing performed by the PJ control conversion section of the control device illustrated in FIG. 2.

FIG. 4 is flowchart outlining processing performed by the PJ control conversion section of the control device illustrated in FIG. 2. First, when an image signal is acquired, the PJ control conversion section 56 starts irradiation image generation processing (step S101).

The calculation section 561 calculates a luminance value at each pixel position on the basis of the acquired image signal and generates a luminance image having the luminance value assigned to each pixel position (step S102).

In step S103 following step S102, the comparison section 562 generates a differential image by comparing the luminance image and a reference image set in advance.

In step S104 following step S103, the computation section 563 generates an irradiation image corresponding to a light quantity distribution of illumination light emitted by the light source device 6, on the basis of the differential image. As a result of the processing in step S104, an irradiation image having a region darker than the reference image and a region brighter than the reference image is generated. The darker region has the light quantity decreased at a position (region) where the luminance value is high in the image signal, and the brighter region has the light quantity increased at a position where the luminance value is low in the image signal.

In step S105 following step S104, the system control section 564 outputs the irradiation image generated by the computation section 563 to the light source control section 62.

Thereafter, the light source control section 62 that has acquired the irradiation image irradiates the subject with the illumination light whose light quantity distribution is commensurate with this irradiation image, thus allowing portions of the subject having a large quantity of reflected light to be irradiated with a small quantity of the illumination light and portions of the subject having a small quantity of reflected light to be irradiated with a large quantity of the illumination light.

Illumination control described above may be performed each time an image signal is input or every several frames.

FIG. 5 is a diagram schematically illustrating examples of images before and after illumination light emission control. (a) of FIG. 5 illustrates the image before the emission control. (b) of FIG. 5 illustrates the image after the emission control. (a) and (b) of FIG. 5 both illustrate an image captured of a same lumen. As illustrated in (a) of FIG. 5, in the image before the emission control, regions $R_1$ and $R_2$ located on a near point side of the lumen have blown-out highlights due to their brightness whereas a region $R_3$ located on a far point side has a blocked-up shadow. In this case, the illumination light is emitted under control of the light source control section 62 on the basis of the image illustrated in (a) of FIG. 5 in such a manner that the light quantity on the near point side (regions $R_1$ and $R_2$) is decreased and the light quantity on the far point side (region $R_3$) is increased. As a result, the image having suppressed brightness on the near point side and increased brightness on the far point side is acquired after the emission control as illustrated in (b) of FIG. 5.

Also, when the apparatus is started, it is possible to set an irradiation range of the illumination light by the endoscope 2 and adjust a shooting range of the imaging section 92 and an irradiation range of the illumination light by performing the above illumination control. For example, an image of a white board or a board with a checkered pattern is captured with the imaging section 92 at the time of white balance adjustment for calibration. At this time, it is possible to adjust misalignment of the illumination position due to an individual difference and uneven illumination caused by characteristics of the optical system by controlling the above light quantity distribution on the basis of the image signal (luminance value at each pixel).

In embodiment 1 described above, the light source device 6 having the projector light source is used to feed back the captured image and perform irradiation with the illumination light whose light quantity has been decreased at the positions where the luminance value is high and whose light quantity has been increased at the positions where the luminance value is low, thus allowing more elaborate control over the light quantity distribution of the illumination light irradiated on the subject.

It should be noted that, although observation using white light has been described as an example in embodiment 1 described above, the present disclosure is also applicable to fluorescent light observation using excitation light or the like. For example, it is possible to adjust the irradiation range and light quantity of the excitation light by performing the illumination light quantity control described above.

Embodiment 2

Figure 6:
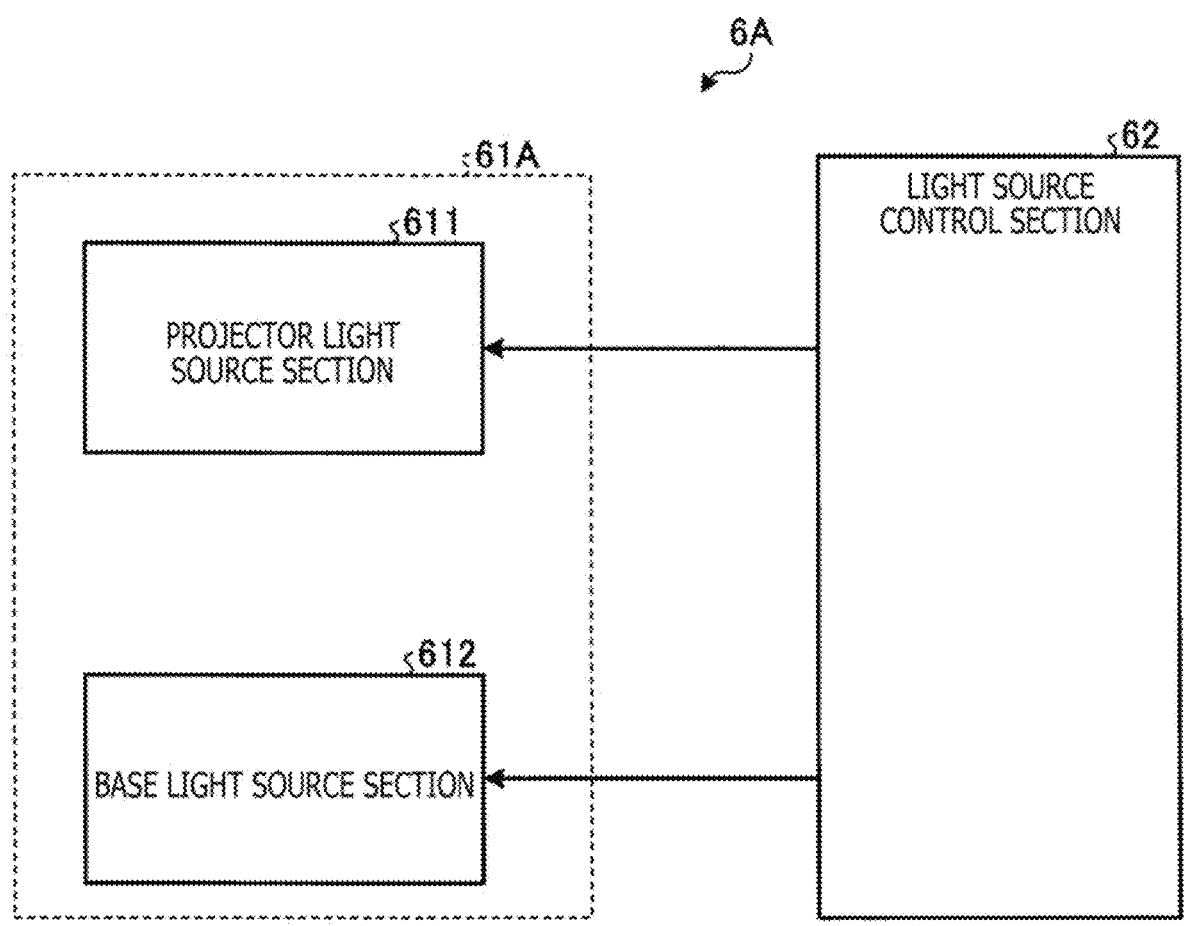
FIG. 6 is a diagram illustrating a configuration of the light source device of the endoscope apparatus according to embodiment 2.

A description will be given next of embodiment 2. FIG. 6 is a diagram illustrating a configuration of the light source device of the endoscope apparatus according to embodiment 2. In embodiment 2, the endoscope apparatus 1 described above includes a light source device 6A in place of the light source device 6. In embodiment 2, the endoscope apparatus 1 is the same as that of embodiment 1 described above except for the configuration of the light source device 6A, and therefore, the redundant description will be omitted.

One end of the light guide 7 is connected to the light source device 6A, and the light source device 6A includes a light source section 61A and a light source control section 62A. The light source section 61A supplies, for example, white light for illuminating the inside of the living body to the one end of the light guide 7. The light source control section 62A controls emission of illumination light by the light source section 61A.

The light source section 61A includes a projector light source section 611 and a base light source section 612.

The projector light source section 611 includes a projector light source. The projector light source includes a light source, a projection element, and an optical system. The light source emits white light. The projection element is a DMD, a liquid crystal panel, or the like. The optical system emits projected light externally. The projector light source section 611 allows adjustment of a projected image of the projection element under control of the light source control section 62 as with the light source section 61 described above.

The base light source section 612 has a light source and an optical system. The light source emits white light. The optical system emits this white light externally. The base light source section 612 emits white light having what is generally called a gaussian distribution or a top-hat intensity distribution. The gaussian distribution is a distribution commensurate with the characteristics of the light source and centered around an optical axis and whose light quantity continuously decreases with increasing distance from the optical axis.

The light source control section 62 causes the light source to emit white light and controls a light projection pattern of the projection element of the projector light source section 611 in such a manner as to match the irradiation image acquired from the system control section 564, on the basis of an instruction from the system control section 564. This provides a brightness (light quantity) distribution of the illumination light emitted from the light source device 6 that is commensurate with the irradiation image.

Also, the light source control section 62 can perform ordinary illumination with white light by causing only the base light source section 612 to emit white light.

Further, the light source control section 62 may cause the base light source section 612 to emit white light and also cause the projector light source section 611 to emit white light only to portions for which the light quantity is desired to be increased, thereby interpolating the light quantity in the distribution of the base light source section 612.

In embodiment 2 described above, the light source device 6A including the projector light source section 611 is used to feed back the captured image and perform irradiation with the illumination light whose light quantity has been decreased at the positions where the luminance value is high and whose light quantity has been increased at the positions where the luminance value is low, thus allowing more elaborate control over the light quantity distribution of the illumination light irradiated on the subject. Further, in embodiment 2, the base light source section 612 is provided to perform irradiation with ordinary white light (e.g., white light having the gaussian light quantity distribution), thus allowing emission of white light from the base light source section 612 when there is no need to control the irradiation pattern.

Embodiment 3

Figure 7:
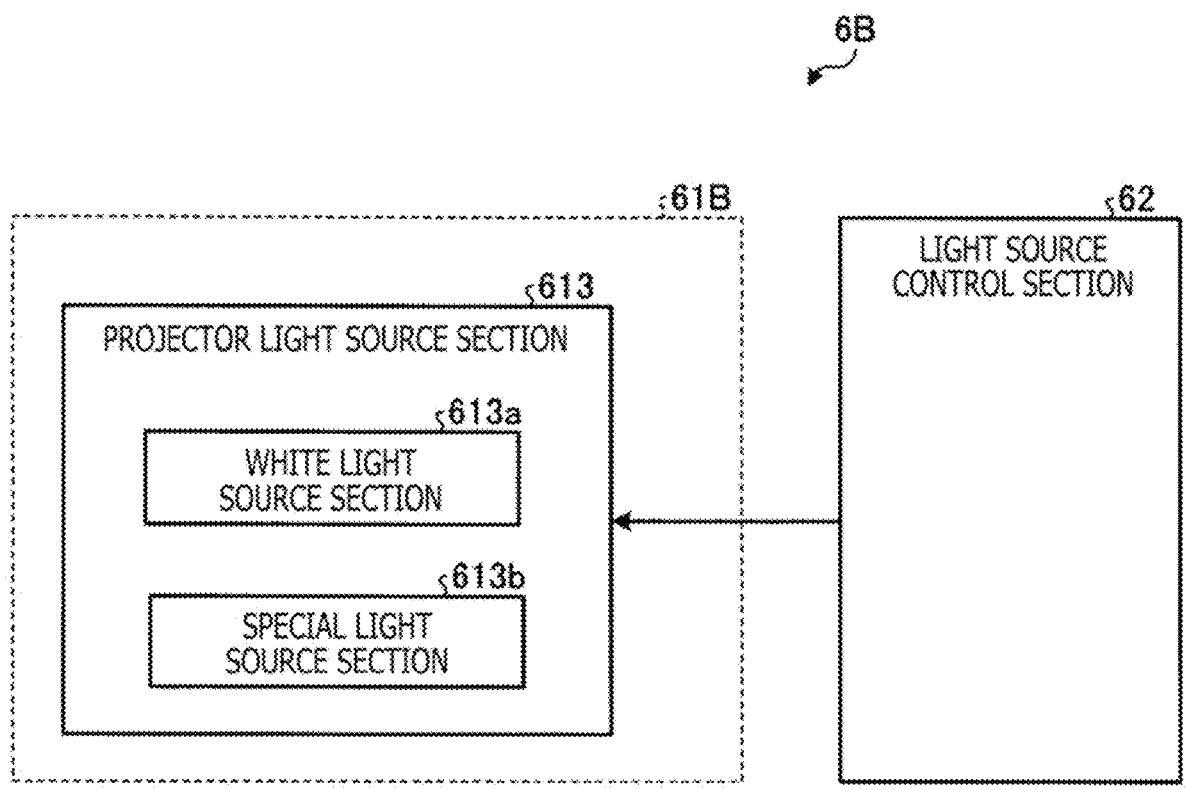
FIG. 7 is a diagram illustrating a configuration of the light source device of the endoscope apparatus according to embodiment 3.

A description will be given next of embodiment 3. FIG. 7 is a diagram illustrating a configuration of the light source device of the endoscope apparatus according to embodiment 3. In embodiment 3, the endoscope apparatus 1 described above includes a light source device 6B in place of the light source device 6. In embodiment 2, the endoscope apparatus 1 is the same as that of embodiment 1 described above except for the configuration of the light source device 6B, and therefore, the redundant description will be omitted.

One end of the light guide 7 is connected to the light source device 6B, and the light source device 6B includes a light source section 61B and the light source control section 62. The light source section 61B supplies, for example, white light for illuminating the inside of the living body to the one end of the light guide 7. The light source control section 62 controls emission of illumination light by the light source section 61B.

The light source section 61B includes a projector light source section 613.

The projector light source section 613 includes a white light source section 613a and a special light source section 613b. The white light source section 613a and the special light source section 613b both include a projector light source.

The white light source section 613a includes a first light source, a projection element, and an optical system. The first light source emits white light. The projection element is a DMD, a liquid crystal panel, or the like. The optical system emits projected light externally.

The special light source section 613b includes a second light source, a projection element, and an optical system. The second light source emits special light (e.g., excitation light) to be used for special light observation. The projection element is a DMD, a liquid crystal panel, or the like. The optical system emits projected light externally. It should be noted that the special light source section 613b may include only the second light source.

The projector light source section 613 allows adjustment of a projected image of the projection element under control of the light source control section 62.

Here, the special light corresponds to light in wavelength bands to be used for any of the following types of special light observation.

Among different types of special light observation are:

NBI for observing states of blood vessels in an outer layer and deeper layers of a mucous membrane by performing irradiation with narrow-band illumination light in bands having center wavelengths of 415 nm and 540 nm and taking advantage of the difference in absorption of light at different wavelengths by hemoglobin;

IRI for diagnosing presence or absence of blood flow by intravenously injecting an agent called indocyanine green (ICG) having an absorption peak in near infrared light in the vicinity of the wavelength of 805 nm in blood as a contrast agent, performing irradiation with excitation light having the center wavelength in the vicinity of 805 nm, and observing fluorescence from the ICG;

AFI for diagnosing a tumor portion by administering a fluorescent agent into a test subject in advance, performing irradiation with excitation light, observing a fluorescence image generated from the test subject, and observing the presence or absence and shape of the fluorescence image; and PDD for acquiring an image that allows easy distinction between cancer cells and normal cells by taking advantage of a property that, if a patient is caused to take a solution of aminolaevulinic acid (5-ALA), the aminolaevulinic acid is metabolized into blood source (heme) in normal tissues in a body whereas the aminolaevulinic acid is not metabolized and, instead, accumulated as a substance called PpIX which is an intermediate product thereof in cancer cells, and that this PpIX emits red fluorescence (with a peak wavelength of 630 nm) when irradiated with blue light (with a center wavelength of 410 nm).

Figure 8:
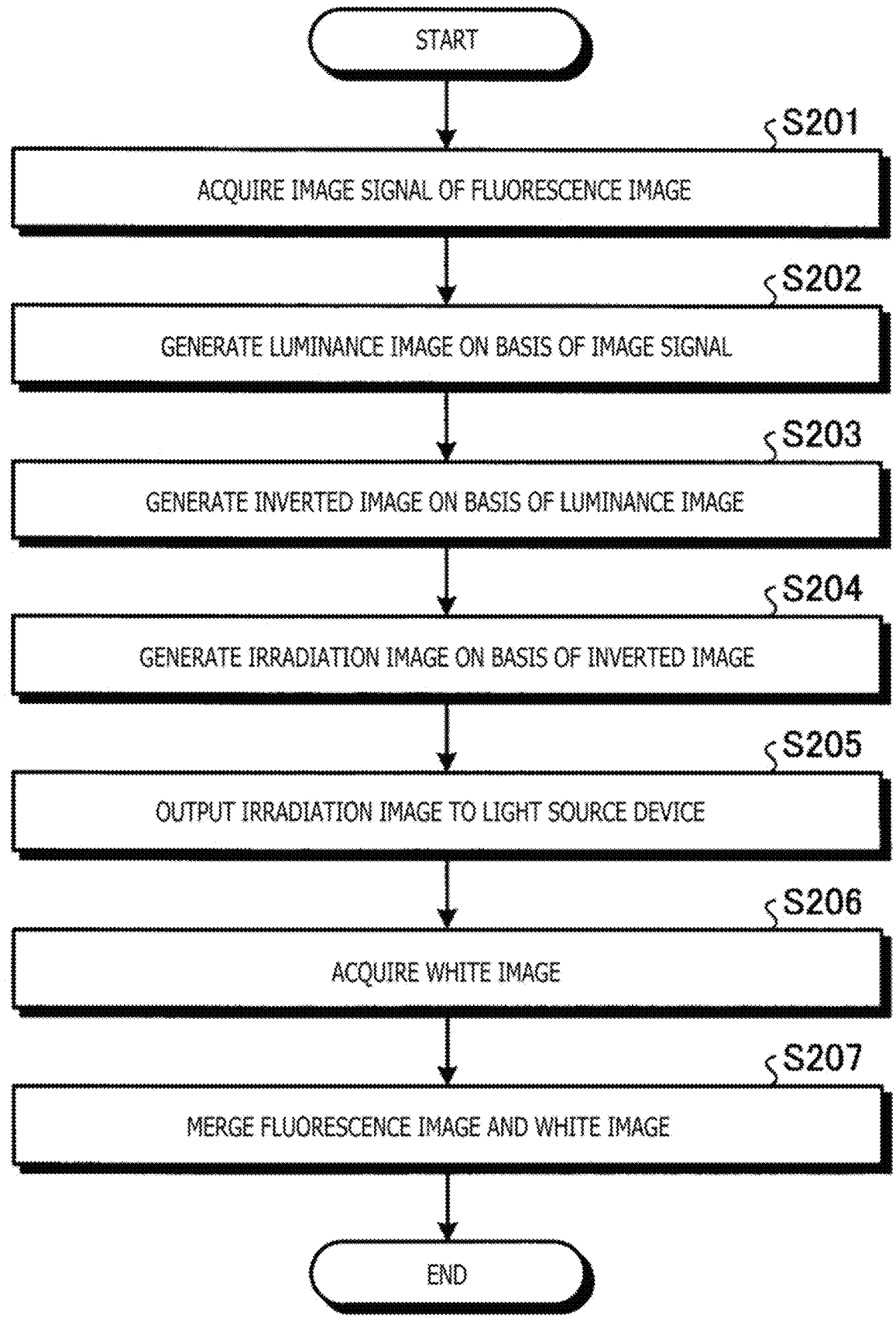
FIG. 8 is flowchart outlining processing performed by the PJ control conversion section in embodiment 3.

A description will be given here of control performed by the PJ control conversion section 56 in embodiment 3. FIG. 8 is flowchart outlining processing performed by the control device in embodiment 3. For example, in the case where a fluorescence image is observed by AFI, the PJ control conversion section 56 acquires an image signal of the fluorescence image by causing the special light source section 613b to perform irradiation with excitation light first (step S201). At this time, the excitation light is irradiated over an entire imaging region.

The calculation section 561 calculates a luminance value at each pixel position on the basis of the image signal of the fluorescence image. The calculation section 561 generates a luminance image having the luminance value assigned to each pixel position on the basis of the calculation result (step S202).

Thereafter, the comparison section 562 generates an inverted image acquired by inverting the luminance values of the luminance image (step S203). The computation section 563 generates an inverted image, for example, by subtracting the luminance values of the luminance image from upper limit luminance values.

Thereafter, the computation section 563 extracts pixels having the luminance values larger than a threshold in the inverted image and generates an irradiation image having a white light irradiation region that includes the extracted pixels (step S204). The threshold at this time corresponds, for example, to a third threshold that is set equal to or larger than a value acquired by inverting a luminance value corresponding to low-luminance noise and smaller than the upper limit value.

The system control section 564 outputs the irradiation image generated by the computation section 563 to the light source control section 62 (step S205). This allows the light source device 6 to perform irradiation with the illumination light (white light) having a light quantity distribution corresponding to the irradiation image, specifically, a light quantity distribution in which a region where the fluorescence image is present is not irradiated with the illumination light.

The signal processing section acquires a white light image using the white light, after which the white light image is processed by the signal processing section 51 and the image processing section 52 (step S206).

Thereafter, the image processing section 52 generates a merged image by merging the white light image and the fluorescence image (step S207). The fluorescence image merged at this time is a transparent image having a color according to the luminance value assigned to a fluorescence detection region and no colors assigned to other regions.

This provides an image that includes the fluorescence image and a background (white light image). The fluorescence image has been excited by the excitation light. The background is included in surroundings of the fluorescence image and represented by reflected light of the white light. At this time, the fluorescence image may be in any color for improved visibility.

FIG. 9 is a diagram schematically illustrating examples of images before and after the illumination light emission control. (a) of FIG. 9 illustrates an example of the fluorescence image. (b) of FIG. 9 illustrates an example of the white light image. (c) of FIG. 9 illustrates an example of the merged image. (a) and (b) of FIG. 9 both illustrate an image captured of a same subject.

When a fluorescence image $G_L$ illustrated in (a) of FIG. 9 is acquired, the calculation section 561 generates a luminance image having luminance values assigned, by using the fluorescence image $G_L$. This allows the luminance image having luminance values assigned to a fluorescence detection region $R_L$ to be generated.

Meanwhile, white light is emitted according to an irradiation image generated on the basis of the luminance image, thus allowing a white light image $G_W$ to be generated with this white light (refer to (b) of FIG. 9). The region of the white light image $G_W$ corresponding to the fluorescence detection region $R_L$ described above has not been irradiated with white light.

The image processing section 52 generates a merged image $G_S$ by merging the fluorescence image $G_L$ and the white light image $G_W$ (refer to (c) of FIG. 9). The merged image $G_S$ is an image in which a color set in advance (color that identifies a fluorescence site) is assigned to the corresponding fluorescence detection region $R_L$ on the white light image $G_W$ described above.

In embodiment 3 described above, the light source device 6B including the white light source section 613a and the special light source section 613b is used to feed back the captured fluorescence image, set the region other than the fluorescence detection region as the white light irradiation region, and perform irradiation with the white light, thus allowing elaborate control over the distribution of types of illumination light irradiated on the subject. According to embodiment 3, it is possible to acquire a merged image represented by fluorescence information alone with no white light component superimposed on the fluorescence site.

Embodiment 4

Figure 10:
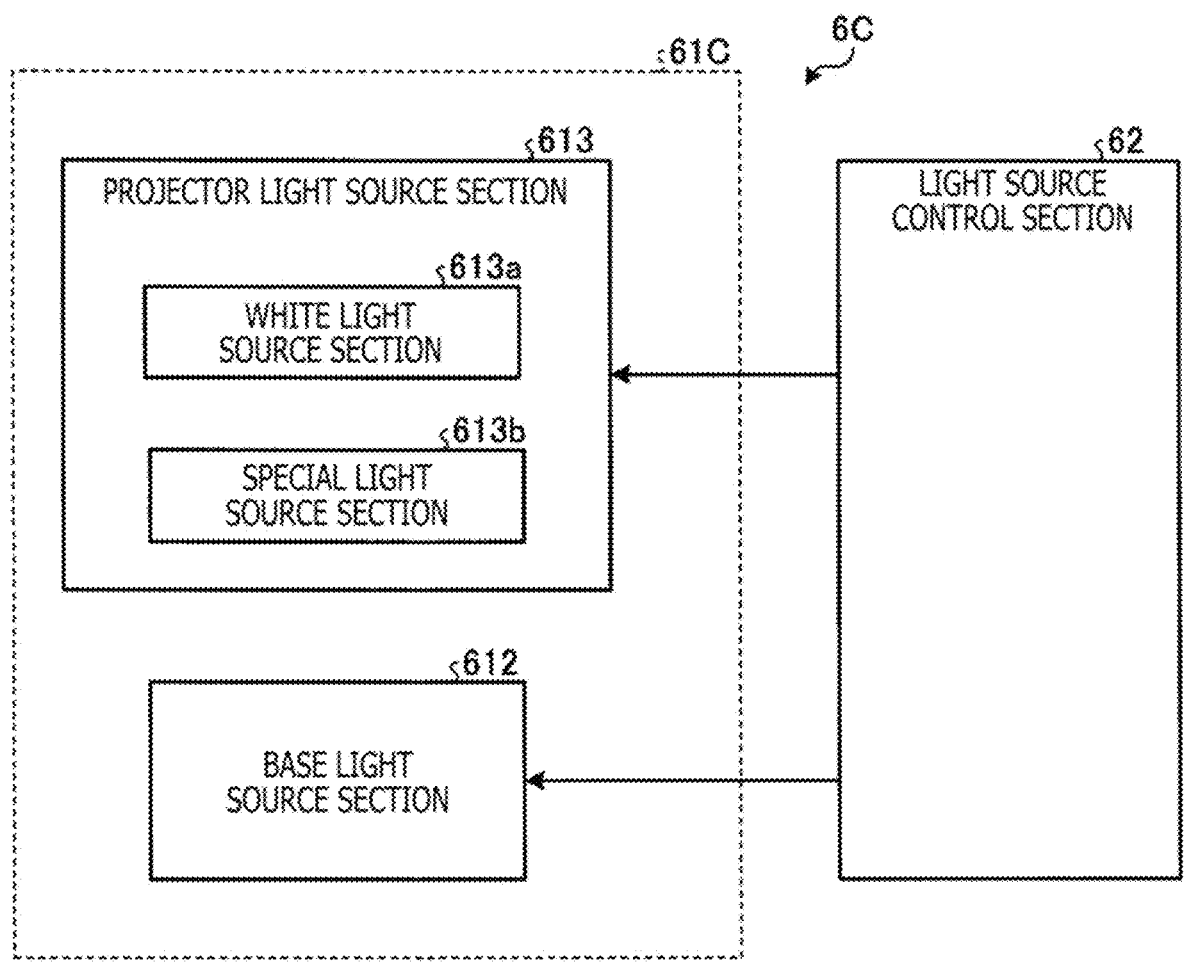
FIG. 10 is a diagram illustrating a configuration of the light source device of the endoscope apparatus according to embodiment 4.

A description will be given next of embodiment 4. FIG. 10 is a diagram illustrating a configuration of the light source device of the endoscope apparatus according to embodiment 4. In embodiment 4, the endoscope apparatus 1 described above includes a light source device 6C in place of the light source device 6. The light source device 6C is configured such that the projector light source section 611 of the light source device 6A according to embodiment 2 is replaced by the projector light source section 613 according to embodiment 3. In embodiment 4, the endoscope apparatus 1 is the same as that of embodiment 1 described above except for the configuration of the light source device 6C, and therefore, the redundant description will be omitted.

One end of the light guide 7 is connected to the light source device 6C, and the light source device 6C includes a light source section 61C and the light source control section 62. The light source section 61C supplies, for example, white light for illuminating the inside of the living body to the one end of the light guide 7. The light source control section 62 controls emission of illumination light by the light source section 61C.

The light source section 61C includes the projector light source section 613 and the base light source section 612. The configurations of the light source sections are the same as those in embodiments 2 and 3, and therefore, the description thereof will be omitted.

The light source control section 62 causes the projector light source section 613 to emit excitation light and white light in set patterns of irradiation images (excitation light irradiation image and white light irradiation image) on the basis of an instruction from the system control section 564.

Also, the light source control section 62 can perform ordinary illumination with white light by causing only the base light source section 612 to emit white light.

Further, the light source control section 62 may cause the base light source section 612 to emit white light and also cause the projector light source section 613 to emit white light only to portions for which the light quantity is desired to be increased, thereby interpolating the light quantity in the distribution of the base light source section 612.

In embodiment 4 described above, the light source device 6C including the white light source section 613a and the special light source section 613b is used to feed back the captured fluorescence image, set the region other than the fluorescence detection region as the white light irradiation region, and perform irradiation with the white light, thus allowing elaborate control over the distribution of types of illumination light irradiated on the subject. According to embodiment 4, it is possible to acquire a merged image represented by fluorescence information alone with no white light component superimposed on the fluorescence site. Further, in embodiment 4, the base light source section 612 is provided to perform irradiation with ordinary white light (e.g., white light having the gaussian light quantity distribution), thus allowing emission of white light from the base light source section 612 when there is no need to control the irradiation pattern.

It should be noted that the special light source section 613b may be provided in the base light source section 612 in embodiment 4.

Other Embodiments

Figure 11:
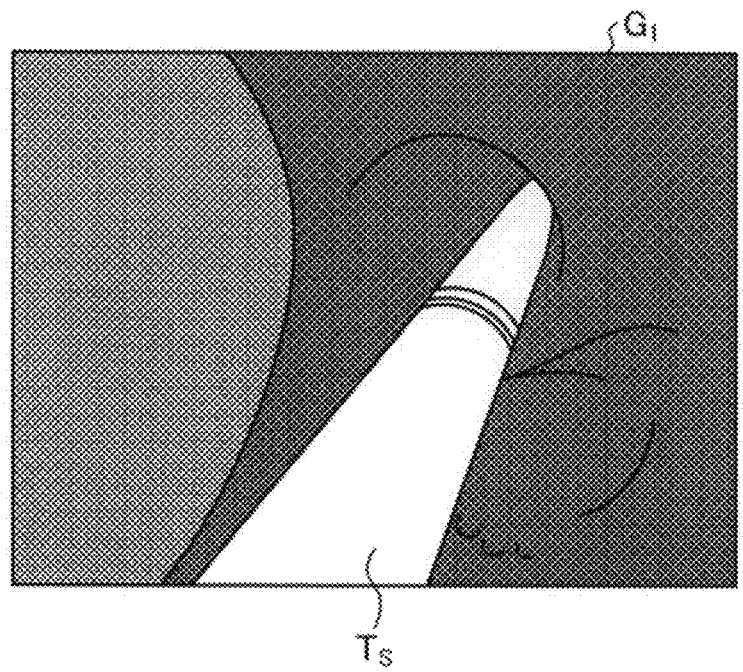
FIG. 11 is a diagram schematically illustrating an example of an image for describing another example 1 of emission control.
Figure 12:
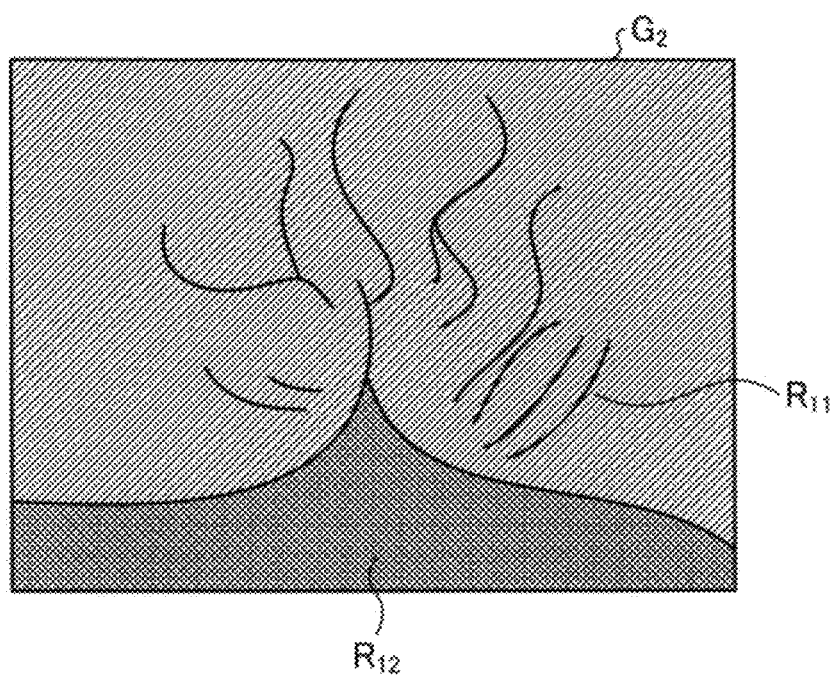
FIG. 12 is a diagram schematically illustrating an example of an image for describing another example 2 of the emission control.

A description will be given next of other embodiments. FIG. 11 is a diagram schematically illustrating an example of an image for describing another example 1 of the emission control. FIG. 12 is a diagram schematically illustrating an example of an image for describing another example 2 of the emission control.

For example, the comparison section 562 identifies a treatment tool $T_S$ by edge detection or other technique and extracts a contour of the treatment tool $T_S$, by using luminance values calculated by the calculation section 561 or the like (refer to FIG. 11). The computation section 563 generates an irradiation image in which the inside of the extracted treatment tool $T_S$ is set as an illumination light non-irradiation region. This prevents irradiation of the treatment tool with the illumination light, thus providing an image in which blown-out highlights due to reflected light from the treatment tool are suppressed.

Also, for example, by using the luminance values calculated by the calculation section 561 or the like, the comparison section 562 performs the edge detection or compares a magnitude relation of the luminance values and color information of the regions with organ information stored in advance to detect an organ, and extracts a region $R_{11}$ where the organ is present (refer to FIG. 12). The computation section 563 generates an irradiation image that is divided into the extracted region $R_{11}$ where the organ is present and a region $R_{12}$ where the organ is absent. The light source control section 62 causes light at different wavelength bands to be emitted to the regions $R_{11}$ and $R_{12}$. For example, the region corresponding to the region $R_{12}$ is irradiated with white light, and the region corresponding to the region $R_{11}$ is irradiated with light at a wavelength band different from that of the white light (e.g., blue or green). In this case, the projection element is preferably a liquid crystal panel. Also, the illumination light irradiated on the region $R_{11}$ is preferably light at a wavelength band that causes the organ to be colored clearly. This provides an image that allows easy identification of the organ.

In addition to the above, control may be performed in such a manner that a bleeding region is extracted from an image, followed by irradiation of the bleeding region with illumination light at a wavelength band that provides coloring that allows easy identification of blood or tissue of the bleeding portion in the image.

Also, control may be performed such that a bacterium is extracted from an image, followed by irradiation of the region where the bacterium is present with illumination light at a wavelength band that provides coloring that allows easy identification of the bacterium in the image.

Also, control may be performed in photodynamic therapy (PDT) such that a treatment range is set, followed by irradiation of only the treatment range with light.

Figure 13:
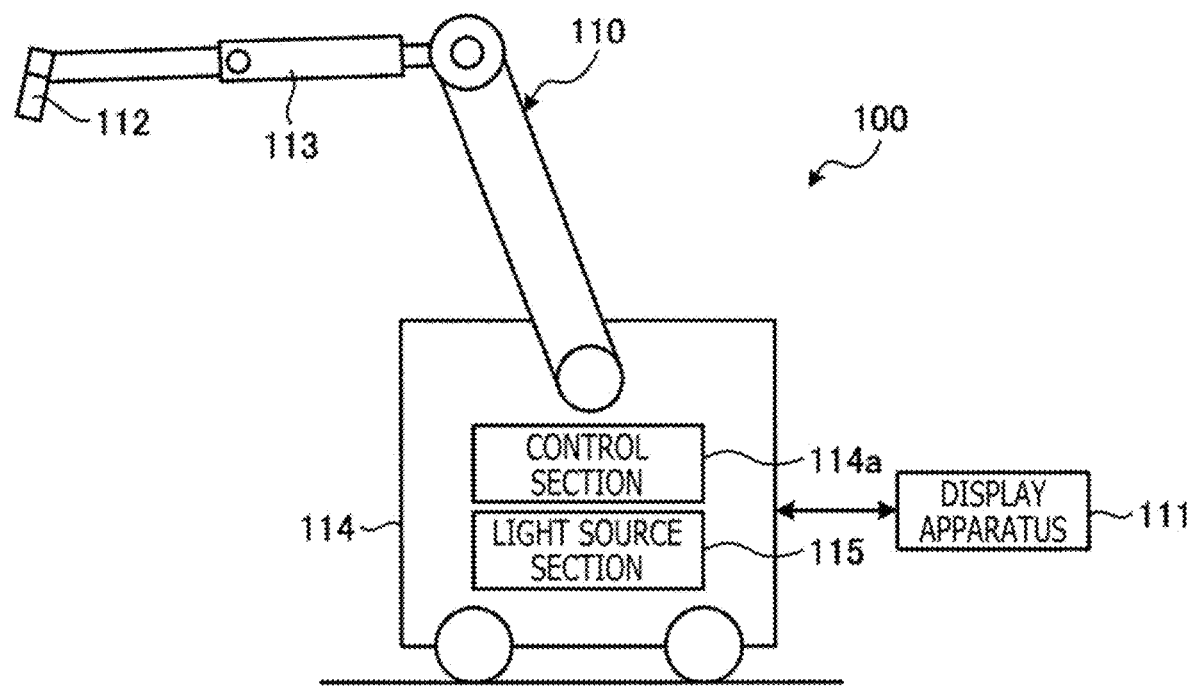
FIG. 13 is a diagram schematically illustrating an overall configuration of a surgical microscope system including a medical observation apparatus according to another embodiment.

Also, although a rigid endoscope is taken as an example in embodiments 1 to 4 described above, the present disclosure may be applied to a soft endoscope and to a surgical microscope system (medical image acquisition system) having a function to enlarge a given field-of-view region, capture an image thereof, and display the captured image. FIG. 13 is a diagram schematically illustrating an overall configuration of a surgical microscope system which is a medical observation system including a medical observation apparatus according to another embodiment.

A surgical microscope system 100 includes a microscope apparatus 110 and a display apparatus 111. The microscope apparatus 110 is a medical imaging apparatus that acquires an image for observation of a subject by imaging. The display apparatus 111 displays the image captured by the microscope apparatus 110. It should be noted that the microscope apparatus 110 and the display apparatus 111 may be integral with each other.

The microscope apparatus 110 includes a microscope section 112, a support section 113, and a base section 114. The microscope section 112 enlarges a microscopic site of the subject and captures an image thereof. The support section 113 is connected to a base end portion of a microscope section 312 and includes an arm that rotatably supports the microscope section 312. The base section 114 rotatably holds a base end portion of a support section v13 and can move on a floor surface. The base section 114 includes a control section 114a and a light source section 115. The control section 114a controls operation of the surgical microscope system 100. The light source section 115 generates illumination light to be irradiated on the subject from the microscope apparatus 110. It should be noted that the control section 114a has the functions of the signal processing section 51, the image processing section 52, the PJ control conversion section 56, and the like described above. Also, the base section 114 may be fixed to a ceiling, a wall surface, or the like to support the support section 113, rather than being provided movably on the floor surface.

The microscope section 112 is, for example, cylindrical in shape and incorporates the imaging section 92 described above. A switch is provided on a side surface of the microscope section 112 to accept an instruction input for operating the microscope apparatus 110. A cover glass (not illustrated) for protecting the inside is provided on an opening surface of a lower end portion of the microscope section 112.

The light source section 115 has the same configuration as any of the light source devices of embodiments 1 to 4 described above.

A user such as a surgeon moves the microscope section 112, manipulates zooming, and switches between illumination light beams while at the same time manipulating various switches with the microscope section 112 held. It should be noted that the microscope section 112 preferably has a shape extending long and narrow in an observation direction to make it easy for the user to hold the microscope section 112 and change a direction of a field of view thereof. Accordingly, the microscope section 112 may be in a shape other than cylindrical and be, for example, in the shape of a polygonal prism.

In the control section 114a, the PJ control conversion section 56 controls the light quantity distribution of the illumination light on the basis of the acquired image signal as in embodiment 1 or the like.

As described above, a similar advantageous effect to that in embodiment 1 described above can be achieved in the surgical microscope system 100.

While embodiments for carrying out the present disclosure have been described so far, the present disclosure should not be limited only by the embodiments described above. While the above embodiments have been described by assuming that the control device 5 handles signal processing and the like, such processing may be handled on the side of the camera head 9.

It should be noted that, while examples have been described in the above embodiments in which the PJ control conversion section 56 generates the irradiation image which is irradiation distribution information and controls the light source device 6 by using the irradiation image, the PJ control conversion section 56 may control the light source device 6 by using information indicating the light quantity distribution of the illumination light, such as information associating pixel coordinates with their light quantity values, as irradiation distribution information.

Also, while examples have been described in the above embodiments in which the PJ control conversion section 56 is provided in the control device 5, the PJ control conversion section 56 may be provided in the light source device 6.

INDUSTRIAL APPLICABILITY

As described above, the medical control device and the medical observation apparatus according to the present disclosure are useful in elaborately controlling the light quantity distribution of the illumination light irradiated on the subject.

REFERENCE SIGNS LIST

1: Endoscope apparatus
2: Endoscope
3: Imaging device
4: Display device
5: Control device
6: Light source device
7: Light guide
8: Transmission cable
9: Camera head
51: Signal processing section
52: Image processing section
53: Communication module
54: Input section
55: Output section
56: Projector control conversion section (PJ control conversion section)
57: Control section
58: Memory
61, 61A to 61C: Light source section
62: Light source control section
91: Lens unit
92: Imaging section
93: Communication module
94: Camera head control section
100: Surgical microscope system
561: Calculation section
562: Comparison section
563: Computation section
564: System control section
611, 613: Projector light source section
612: Base light source section

The invention claimed is:
1. A medical observation apparatus comprising:
an image sensor configured to generate an electric signal by capturing an image of a subject;
processing circuitry configured to
  generate a captured image on a basis of the electric signal generated by the image sensor, and
  generate control information for controlling a light quantity distribution of illumination light, according to a brightness distribution of the captured image;
a first optical system having a first light source that emits white light and a projection element that externally projects the light emitted by the first light source according to the control information;
a second optical system having a second light source that emits special light;
light source control circuitry configured to control emission of illumination light on a basis of the control information, wherein
the processing circuit is further configured to:
  control the control information for setting a projection region of the white light on a basis of a special light image captured by the image sensor with the special light,
  convert the captured image to generate irradiation distribution information indicating the light quantity distribution of the illumination light according to the brightness distribution of the captured image,
  convert a special light image captured with special light into a luminance image having a luminance value assigned to each pixel,
  generate an irradiation image as the irradiation distribution information by inverting the luminance image such that, in the irradiation image, a region in which a luminance value after the inversion is larger than a threshold is set as a white light projection region, and
  generate a merged image obtained by merging the special light image and a white light image captured with white light whose light quantity distribution is commensurate with the irradiation image.

2. The medical observation apparatus of claim 1, further comprising:
a base light source that emits white light.

3. The medical observation apparatus of claim 1, wherein the second optical system includes a second projection element that externally projects the light emitted by the second light source according to the control information, and
the processing circuitry is configured to control the control information for setting a projection region of the special light on a basis of the special light image captured by the image sensor with the special light.

4. A medical control device comprising:
circuitry configured to:
generate a captured image on a basis of an electric signal generated by an imaging device that captures an image of a subject;
generate control information for controlling a light quantity distribution of illumination light, according to a brightness distribution of the captured image;
convert the captured image to generate irradiation distribution information indicating the light quantity distribution of the illumination light according to the brightness distribution of the captured image;
convert a special light image captured with special light into a luminance image having a luminance value assigned to each pixel;
generate an irradiation image as the irradiation distribution information by inverting the luminance image such that, in the irradiation image, a region in which a luminance value after the inversion is larger than a threshold is set as a white light projection region; and
generate a merged image obtained by merging the special light image and a white light image captured with white light whose light quantity distribution is commensurate with the irradiation image.

5. The medical control device according to claim 4, wherein the circuitry is configured to:
convert the captured image to generate irradiation distribution information indicating the light quantity distribution of the illumination light according to the brightness distribution of the captured image;
convert the captured image into a luminance image having a luminance value assigned to each pixel; and
generate, as the irradiation distribution information, an irradiation image in which a projection luminance of a region in which the luminance value is larger than a first threshold is decreased to below a reference luminance set in advance and a projection luminance of a region in which the luminance value is smaller than a second threshold is increased to above the reference luminance.

\* \* \* \* \*